United States Patent [19]

Judet, deceased et al.

[11] 4,365,358
[45] Dec. 28, 1982

[54] JOINT PROSTHESES, PARTICULARLY IN HIP PROSTHESES

[76] Inventors: Robert Judet, deceased, late of Paris, France; by Vincent Judet, administrator, 17, Boulevard de Montmorency, 75016 Paris, France

[21] Appl. No.: 66,842

[22] Filed: Aug. 15, 1979

[30] Foreign Application Priority Data

Aug. 18, 1978 [FR] France .................. 78 24094

[51] Int. Cl.³ .................................. A61F 1/03
[52] U.S. Cl. ....................... 3/1.912; 128/92 C
[58] Field of Search ............ 128/92 C, 92 CA; 3/1.9, 3/1.91, 1.911, 1.912, 1.913

[56] References Cited

U.S. PATENT DOCUMENTS

| Re. 28,895 | 7/1976 | Noiles ............... | 3/1.912 |
| 3,863,273 | 2/1975 | Averill ............... | 3/1.91 |
| 3,903,549 | 9/1975 | Deyerk ............... | 3/1.912 |
| 4,051,559 | 10/1977 | Pifferi ............... | 3/1.912 |
| 4,172,296 | 10/1979 | D'Errico ............. | 3/1.91 X |

FOREIGN PATENT DOCUMENTS 1325534  8/1973  United Kingdom ............. 3/1.912

Primary Examiner—Clifford D. Crowder
Attorney, Agent, or Firm—Darby & Darby

[57] ABSTRACT

A surgical prostheses comprising a base piece and a joint piece formed by an outer casing within which is located a piece of synthetic material which holds a pivotable joint into which the base piece is to be inserted. Means are provided so that the piece of synthetic material can be removed from the casing.

3 Claims, 3 Drawing Figures

U.S. Patent     Dec. 28, 1982     4,365,358
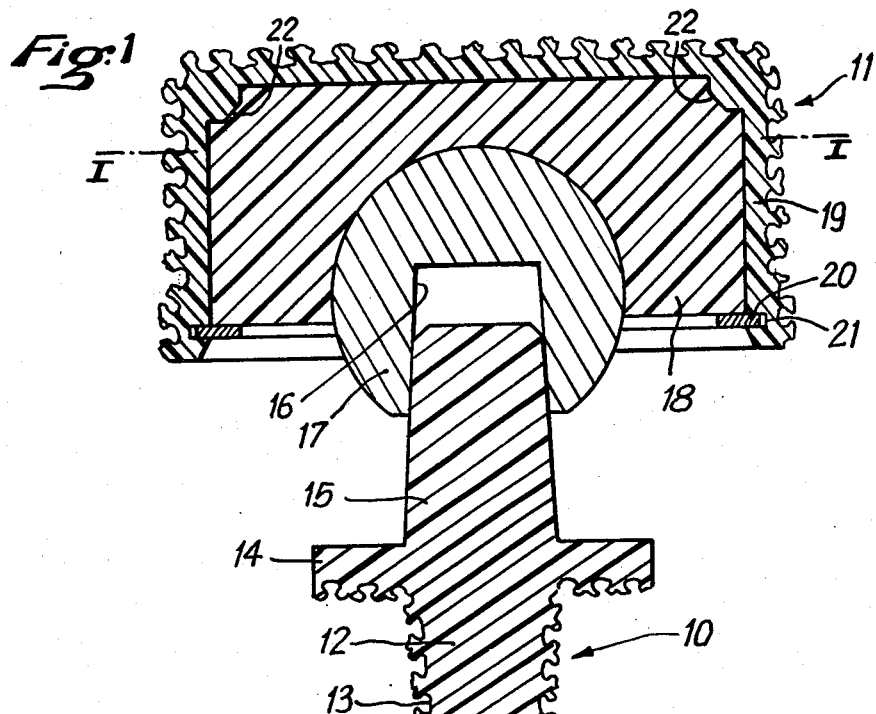
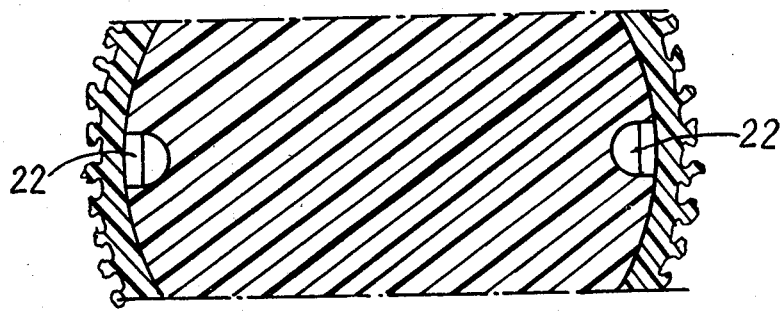
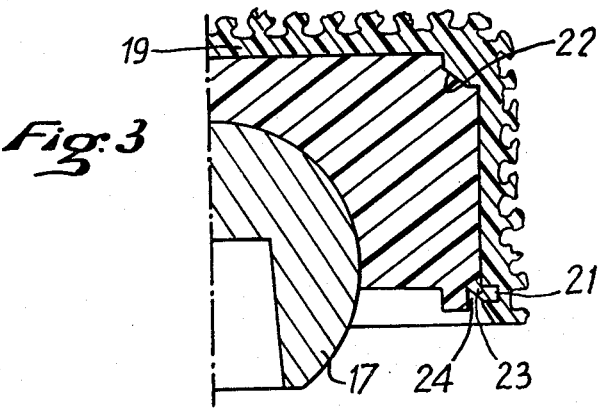

JOINT PROSTHESES, PARTICULARLY IN HIP PROSTHESES

The present invention relates to surgical prostheses and more particularly to prostheses intended to replace osseous joints, for example, like that of the hip.

The prostheses commonly used are made of a metal alloy compatible with the organic tissues of the human body. However, their attachment to the osseous walls have posed problems difficult to solve. In fact, it is often necessary to add a binder, such as a cement or a glue, to obtain a proper union between the prosthesis and the osseous wall in which it is to be embedded. It then happens that either the cement is not well tolerated by the body or in the long run it is more or less dissolved or degraded and the prosthesis is no longer held firmly enough. The binder can be replaced by mechanical fastening means, such as screws, but this is not always possible to accomplish in a simple and safe manner.

From the work of the applicant it is known how to make the surface of metallic prostheses with a plurality of small cavities and rugosities into which the bone intrudes in the process of osteosynthesis. This results in the prosthesis becoming intimately integral with the bone.

Thus one can, in particular, make hip prostheses, formed of two parts articulated together. The first, called the "base", is driven into the upper portion of the femur, the head of which has previously been sectioned. The base is formed at its upper end with a spherical piece, intended to replace the head of the femur. The second part, called "cotyle", is formed by a cylindrical metal casing, intended to be inserted in a hollow cylindrical seat in the iliac bone. A piece of a composition of synthetic material is secured in the casing, which includes a spherical seat in which is encased the spherical piece of the first part. To prevent the synthetic composition from becoming loose, with wear, relative to its metallic seat, the two pieces are pre-assembled in the shop by force fitting under a pressure usually of several tons.

Over a long period, the spherical head of the first part can wear the synthetic composition in which it is embedded. While it is possible to remove the worn synthetic composition from its seat, it is difficult to put a new one in its place while the prosthesis is in the patient because such assembly can properly be made only under a pressure of several tons. It is then necessary to extract from the bone the entire piece called "cotyle" to replace it. But when this piece has a surface presenting a plurality of small alveoles and rugosities, it is so intimately connected to the bone that it is impossible to extract it therefrom without boring in the bone a seat of greater dimensions. The change of the cotyle then becomes a delicate operation, which, moreover, cannot be repeated very often.

The object of the invention is to remedy this disadvantage by providing a prosthesis in which the piece of material of synthetic composition is removable from the casing.

By way of non-limiting example, and to facilitate the comprehension of the invention, the annexed drawings show FIG. 1, a sectional view of a cotyle according to the invention;

FIG. 2, a partial view in section along I—I of FIG. 1; and

FIG. 3, a half-view in section of a further embodiment.

Referring to the drawings, the hip prosthesis includes a piece 10, called the base, and a piece 11, called cotyle. Base 10 is formed by a rod 12 whose surface presents a plurality of alveoli 13, which are preferably undercut. The rod 12 is intended to be driven into the femur. A collar 14 is formed on the base to support the base on the surface of the bone. Collar 14 is topped by a slightly conical nipple 15, on which is fitted a sphere 17 having a seat 16 of matching form for nipple 15. Sphere 17 is retained in a matching spherical seat, formed in a piece of synthetic composition 18 which is held in a cylindrical metallic casing 19 of the cotyle. The inner wall of casing 19 is smooth and the outer wall is shaped like that of rod 12 with a plurality of undercut alveoli.

Because of the corrugated structure of the outer surface of the casing 19, which is generally cylindrical and cup-shaped, with the bone intruding into the cavities, it is practically impossible to remove this piece once it has been attached to the base. This may present a serious disadvantage if the piece of the synthetic composition 18 which retains the ball 17 deteriorates.

According to the present invention, the diameter of the pieces of the composition 18 is made slightly smaller than that of the inner wall of the casing 19 so that the piece 18 can be introduced under gentle friction into said casing 19. The piece of composition 18 is maintained in place in the casing 19 by means of a circlip or spring 20 disposed in a groove 21 formed in casing 19. The piece of composition 18 has at its base two recesses which are to be seated against two flat pieces 22 arranged in the bottom of the casing. Thus, the piece of composition 18 cannot pivot inside the casing 19 and it cannot fall out since it is held by clip 21.

To replace the piece 18, when it is worn, it is only necessary to remove the circlip 20. The composition 18 and ball 17 can then be easily removed and replaced.

FIG. 3 shows a further embodiment of the invention according to which the piece 18 has at the level of the groove 21 an oblique lip 23 which, when the piece 18 is put in place, snaps into the groove 21.

Mechanical strength tests have shown that where the piece 18 is held by lip 23, to extract the piece from its seat by deforming the lip 21, a force in the order of 150 kg is required. Thus, it is certain that the composition 18 cannot come out of its seat accidentally. However, to remove it on the operating table, it is only necessary to cut it by means of a special tool passing through the peripheral groove 24 provided for that purpose at the base of the lip 23.

In the examples shown, the casing 19 and the pieces 18 are cylindrical. It should be understood that the invention is not limited to this particular shape and these pieces may be polygonal, or have at least one flat wall in which case the projecting pieces 22 are no longer necessary.

I claim:

1. A hip joint prosthesis comprising
    a base for engaging the prosthesis with a femur,
    means on said base for engaging the base to the femur,
    a cotyle for engaging the prosthesis with a hip bone,
    means on said cotyle for engaging it to the hip bone,
    an articulating hip joint for connection between said cotyle and said base, said hip joint including a peripheral severable lip for engagement with a complementary groove at an inner face of said cotyle, means for providing access by a severing device to said lip, said base being formed with a shank at one end terminating in an outwardly extending collar, said femur engaging means comprising a plurality of alveoli on the outer surface of said shank and on the lower surface of said collar for engagement with the osseous matter of a femur bone.

2. A hip joint prosthesis comprising a base, for engaging the prosthesis with a femur, said base provided with an axially projecting nipple, means on the base for engaging the base to the femur, a cotyle, for engaging the prosthesis with a hip bone, means on the cotyle for engaging the cotyle to the hip bone, a hip joint, including a block of resilient material having dimensions to provide a pressure engagement within the cotyle and a relatively centrally located, generally spherical seat, a generally spherical ball complementary with said spherical seat and rotatably engaged at said seat, said ball including a channel for engagement with said nipple, said cotyle including at least one groove at an inner face, said groove complementary to a severable lip at a peripheral portion of said hip joint block, whereby the block is maintained within the cotyle by the pressure fit and engagement of the lip and groove, and means for providing access by a severing device to the severable lip.

3. A hip joint prosthesis according to claim 2 wherein the means for providing access by a severing device comprises in the block a peripheral groove adjacent to the inner edge of the lip.

* * * * *